United States Patent [19]

Anger

[11] 4,197,460
[45] Apr. 8, 1980

[54] MULTI-ANGLE NUCLEAR IMAGING APPARATUS AND METHOD

[75] Inventor: Hal O. Anger, Berkeley, Calif.

[73] Assignee: The United States of America as represented by the United States Department of Energy, Washington, D.C.

[21] Appl. No.: 767,886

[22] Filed: Feb. 11, 1977

[51] Int. Cl.² .................................................. G01T 1/20
[52] U.S. Cl. .................................................. 250/363 S
[58] Field of Search ........................... 250/363 S, 445 T

[56] References Cited

U.S. PATENT DOCUMENTS

| | | | |
|---|---|---|---|
| 3,688,113 | 8/1972 | Miraldi | 250/445 T X |
| 3,979,594 | 9/1976 | Anger | 250/363 S X |
| 3,988,585 | 10/1976 | O'Neill et al. | 250/363 S |

Primary Examiner—Davis L. Willis
Attorney, Agent, or Firm—R. V. Lupo; Randall G. Erdley; Harold C. Hohbach

[57] ABSTRACT

Nuclear imaging apparatus for obtaining multi-plane readouts of radioactive material in a human or animal subject. A probe disposed in the vicinity of the subject is provided for receiving radiation from radiating sources in the subject and for forming a probe radiation image. The probe has a collimator with different portions thereof having holes disposed at different angles. A single scintillation crystal overlies the collimator for receiving radiation passing through the collimator and producing scintillations to provide the probe image. An array of photomultiplier tubes overlie the single crystal for observing the probe image and providing electrical outputs. Conversion apparatus is provided for converting the electrical outputs representing the probe image into optical images displayed on the screen of a cathode ray tube. Divider apparatus is provided for dividing the probe radiation image into a plurality of areas with the areas corresponding to different portions of the collimator having holes disposed at different angles. A light sensitive medium is provided for receiving optical images. Apparatus is provided for causing relative movement between the probe and the subject. Apparatus is also provided for causing relative movement between the optical image on the screen and the light sensitive medium which corresponds to the relative movement between the probe and the subject whereby there is produced on the light sensitive medium a plurality of images that portray the subject as seen from different angles corresponding to the portions of the collimator having holes at different angles.

20 Claims, 11 Drawing Figures

FIG.—1

IMAGE DETECTOR FIELD IS
DIVIDED ELECTRONICALLY
INTO SEVEN AREAS

FIG.—2

SEVEN AREAS ARE SPACED APART AND
MINIFIED ON CRT DISPLAY

FIG.—3

SEVEN AREAS ARE SCANNED IN SYNCHRONISM
WITH IMAGE DETECTOR PROBE

COLLIMATOR SECTIONS  A: HOLES ANGLED TOWARD PATIENTS HEAD
B: HOLES ANGLED TOWARD PATIENTS LEFT
C: HOLES NORMAL TO COLLIMATOR
D: HOLES ANGLED TOWARD PATIENTS RIGHT
E: HOLES ANGLED TOWARDS PATIENTS TOES

MULTI-ANGLE NUCLEAR IMAGING APPARATUS AND METHOD

The Government has rights in this invention pursuant to Contract No. 7405-ENG-48 awarded by the U.S. Energy Research and Development Administration.

BACKGROUND OF THE INVENTION

In U.S. Pat. No. 3,329,814 there is disclosed a stereo positron camera for determining the spatial distribution of radioactive material in a test body. The camera utilizes a large scintillation disc which is provided on one side of the subject. A two-dimensional array of phototubes is provided for detecting scintillations in the scintillation disc. A pair of spaced apart relatively small right and left scintillators are provided on the other side of the subject. A photomultiplier is provided for each of the right and left scintillators. The large scintillator and the two small scintillators are provided for ascertaining when concurrent signals are received by the large scintillator disc and one of the small scintillator discs. In addition, means is provided for ascertaining when concurrent signals are received from the main or large scintillation disc and the other of the small scintillators to provide a stereo view of the gamma rays emitted by the positron annihilations. Thus it can be seen that the camera disclosed in U.S. Pat. No. 3,329,814 is limited to an arrangement in which gamma rays are emitted at approximately 180° with respect to each other. In addition, no scanning capability is provided.

At the present time, there are many cameras in use which are sensitive to gamma rays but which are not used with positrons. In such cameras, a need has arisen for providing imaging apparatus which is capable of providing images from different angles of the patient. This is particularly important where there may be overlying bony structure, other organs and the like which make it difficult to obtain a clear picture of the radiation image of the subject being examined. There is therefore a need for a multi-angle nuclear imaging apparatus and method which will overcome these difficulties.

U.S. Pat. No. 3,988,585 issued on Oct. 25, 1976 has recently come to applicant's attention. It is unknown at this time whether the disclosure contained therein constitutes prior art with respect to the present application.

Summary of the Invention and Objects

The multi-angle nuclear imaging apparatus of the present invention is utilized for obtaining readouts of radiation sources located in different positions in the subject. The apparatus comprises a probe disposed in the vicinity of the subject for receiving radiation from the subject and for forming a probe radiation image. The probe has a collimator with different portions thereof having holes in each portion being disposed at different angle from the holes in another portion. A single crystal overlies the collimator for receiving radiation passing through the collimator and producing scintillations where the radiation impinges the crystal to form the probe radiation image. Means is provided for converting the probe radiation image into an optical image displayed on the screen of a cathode ray tube. Means is provided for dividing the probe radiation image into a plurality of areas corresponding to the different portions of the collimator. A light sensitive medium is provided for receiving the optical images on the screen. Means is provided for causing relative movement between the probe and the subject. Means is also provided for causing relative movement between the optical image on the screen and the light sensitive medium which corresponds to the relative movement between the probe and the subject whereby there is provided on the light sensitive medium a plurality of images that portray the subject as seen from different angles.

In general, it is an object of the present invention to provide a nuclear imaging apparatus and method which is capable of providing images of a subject as seen from different angles.

Another object of the invention is to provide an apparatus and method of the above character in which the images at different angles can be obtained during a single scan.

Another object of the invention is to provide an apparatus and method of the above character which can be utilized with whole body scanning.

Another object of the invention is to provide an apparatus and method of the above character which can utilize either optical or electrical means for dividing the probe radiation image into a plurality of multi-angle images.

Another object of the invention is to provide an apparatus and method of the above character which permits the observer to see around overlying objects which might obstruct deeper lying objects.

Another object of the invention is to provide an apparatus and method of the above character which gives information on the relative depth of objects.

Another object of the invention is to provide an apparatus and method of the above character which is particularly useful with all kinds of organs and for tumor scanning.

Another object of the invention is to provide an apparatus and method of the above character which makes it possible to estimate the true size of organs that are angularly rotated from their normal position.

Another object of the invention is to provide an apparatus and method of the above character in which the additional multi-angle images can be obtained without an increase in the scanning time while obtaining conventional tomographic images.

Another object of the invention is to provide an apparatus and method of the above character in which adjacent images can be observed as stereo pairs.

Additional objects and features of the invention will appear from the following description in which the preferred embodiments are set forth in detail in conjunction with the accompanying drawings.

DESCRIPTION OF THE PREFERRED EMBODIMENTS

Figure 1:
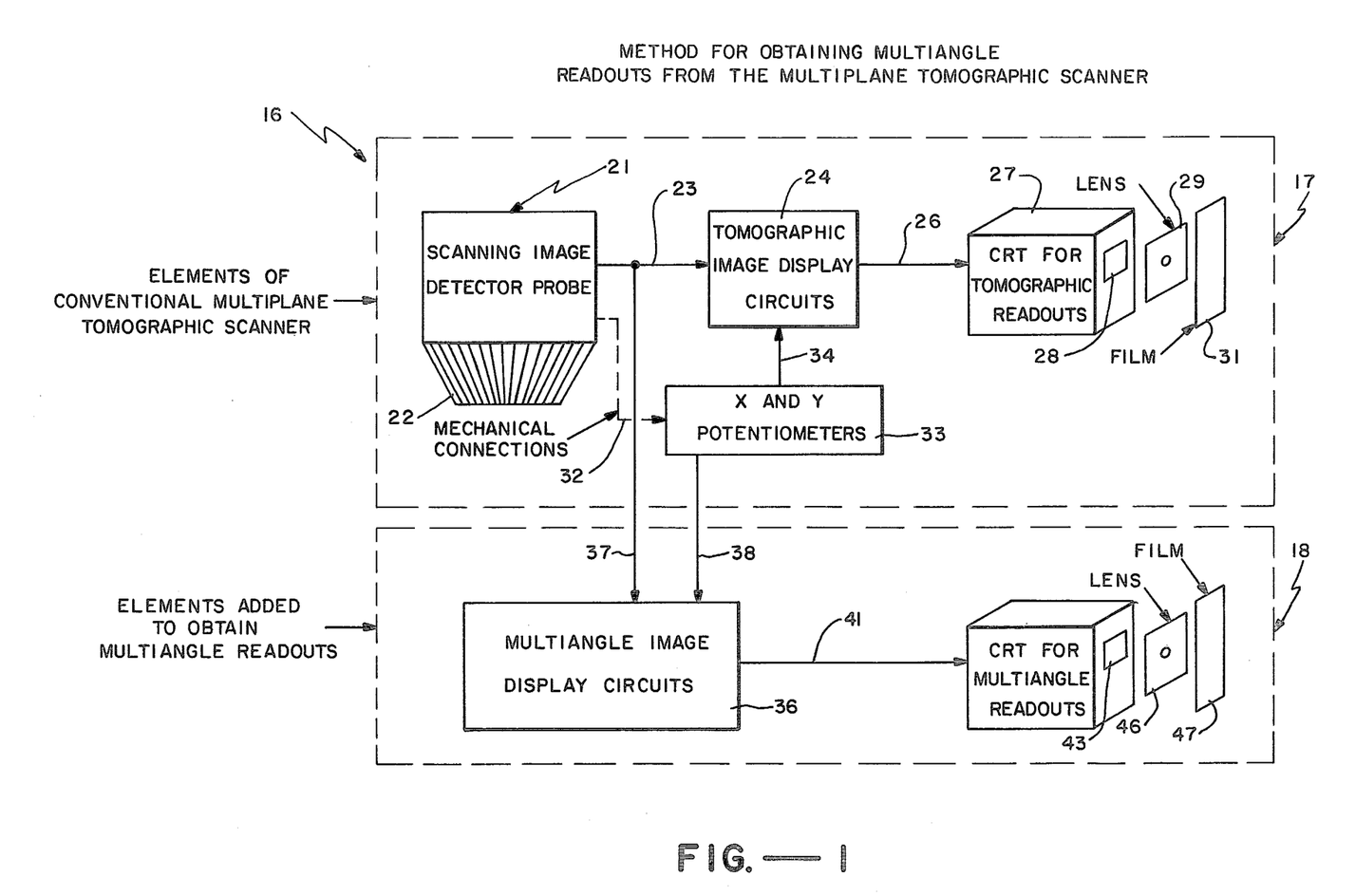
FIG. 1 is a block diagram of a multi-angle nuclear imaging apparatus and method incorporating the present invention and particularly shows what is required to be added to a conventional tomographic scanner to provide the multi-angle readouts.

The multi-angle nuclear imaging apparatus and the method comprising the present invention can be described in conjunction with FIG. 1 in which a large block 17 shows the elements which comprise the conventional multi-plane tomographic scanner of the type described in U.S. Pat. No. 3,979,594 and a large block 18 which shows the elements which must be added to such a conventional multi-plane tomographic scanner to obtain the multi-angle readouts of the present invention.

As shown in FIG. 1, the large block 17 consists of a scanning image detector probe 21. As described in U.S. Pat. No. 3,979,594 such a probe includes a focused collimator 22. It also includes a single large scintillation crystal having an 8½ inch diameter sodium iodide crystal (not shown) and an array in the form of a plurality i.e. seven photomultiplier tubes (not shown) lying in an xy plane parallel to the plane of the crystal which overlie the scintillation crystal and are adapted to observe scintillations occurring in the crystal. As disclosed in U.S. Pat. No. 3,979,594, the probe 21 is adapted to be positioned in the vicinity of the subject to be observed. The subject which for example may be a portion of the human body or of an animal has been treated so that it has disposed therein a three dimensional distribution of a radioactive material which forms sources of gamma rays. The gamma rays emitted from the subject impinge upon the probe and pass through the focused collimator 22 and impinge upon the scintillation crystal to form individual scintillations to provide a probe radiation image showing the distribution of the radiation impinging upon the scintillator. The photomultiplier tubes within the probe sense the scintillations and create x and y coordinate signals as described in U.S. Pat. No. 3,011,057 which are supplied as shown by the line 23 to a block 24 entitled "tomographic image display circuits". These tomographic image display circuits 24 are of a conventional type such as those utilized by Searle Analytic in the Pho/Con tomographic scanner. The information provided by the tomographic image display circuits is supplied over a line 26 to a cathode ray tube apparatus 27 to provide tomographic readouts on a screen 28. By utilizing the electronic circuitry to obtain tomographic images, the single lens 29 which is provided can be stationary as well as the light sensitive medium in the form of film 31 for recording the tomographic images.

Alternatively, if desired, and as described in said U.S. Pat. No. 3,979,594, instead of having the electronic circuitry provide the tomographic scanning, the same results can be obtained by moving the film in synchronism with the relative rectilinear scanning movement between the probe and the subject and by utilizing a multi-lens system in which each of the lenses is focused for a different depth. In either arrangement, mechanical information must be obtained from the relative movement between the probe and the subject and this is supplied through the mechanical connections represented by the dotted line 32 in FIG. 1 which supplies position information to x and y potentiometers represented by the block 33. This information in the embodiment shown in FIG. 1 is supplied to the tomographic image display circuits 24 through the line 34. Where the tomographic effect is obtained by scanning the film utilizing the multi-element lens system, the film movement mechanism is supplied with information from the x and y potentiometers 33.

Thus, it can be seen that the large block 17 provides the conventional tomographic images which are obtained from the multi-plane tomographic scanner of the type described in U.S. Pat. No. 3,979,594. In the large block 18 there is shown the additional elements which must be added to obtain a multi-angle readout. As shown therein, it consists of a block 36 which is identified as "multi-angle image display circuits" which receives x and y coordinate information on line 37 from the probe 21 as well as information on line 38 from the x and y potentiometers 33 using the relative positions between the probe and the subject. The multi-angle image display circuits 36 can be of a conventional type and are utilized for electronically dividing the probe radiation image into a plurality of areas as for example the seven areas shown in FIG. 2.

Figures 2, 3:
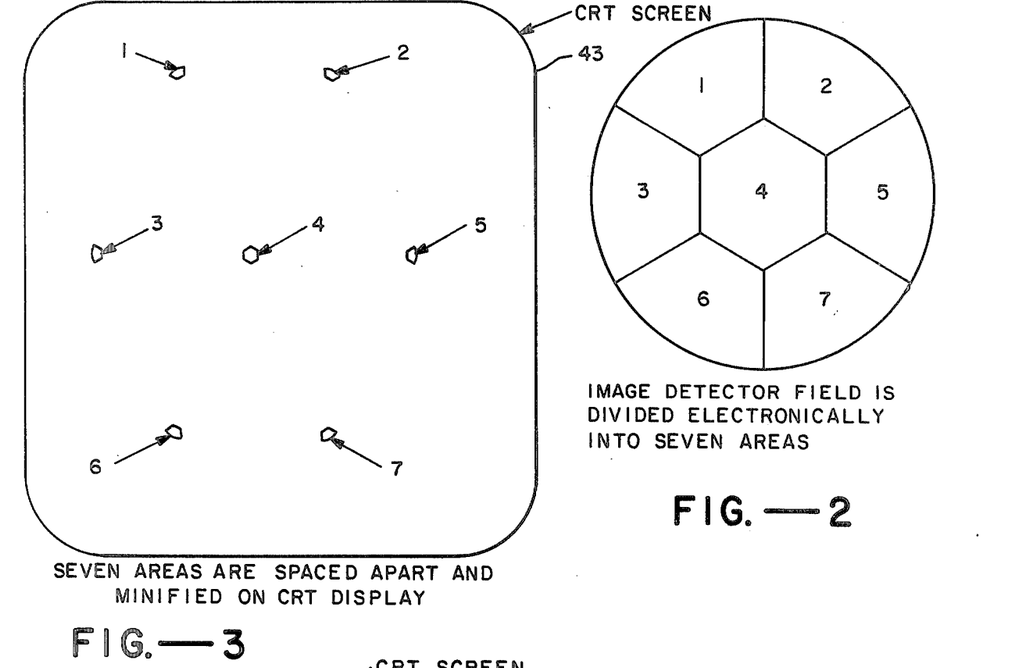
FIG. 2 is a plan view of the image detector field provided in the probe and shows the manner in which it can be electronically divided into a plurality of areas.
FIG. 3 is a view of the cathode ray tube screen and shows the plurality of areas in FIG. 2 spaced apart and minified.

The central area 4 of the seven areas is in the form of a six-sided polygon or hexagon. Areas 1, 2, 3, 5, 6 and 7 of these seven areas surround this central area 4. These seven areas are separated electronically and minified and this information is supplied over a line 41 to a cathode ray tube display apparatus 42 which is provided with a cathode ray tube having a screen 43. As can be seen from FIG. 3, the seven probe image areas are minified and displayed in spaced apart positions on the screen. Each of the seven areas on the cathode ray tube are scanned slowly in synchronism with the relative movement between the probe 21 and the subject.

Figure 4:
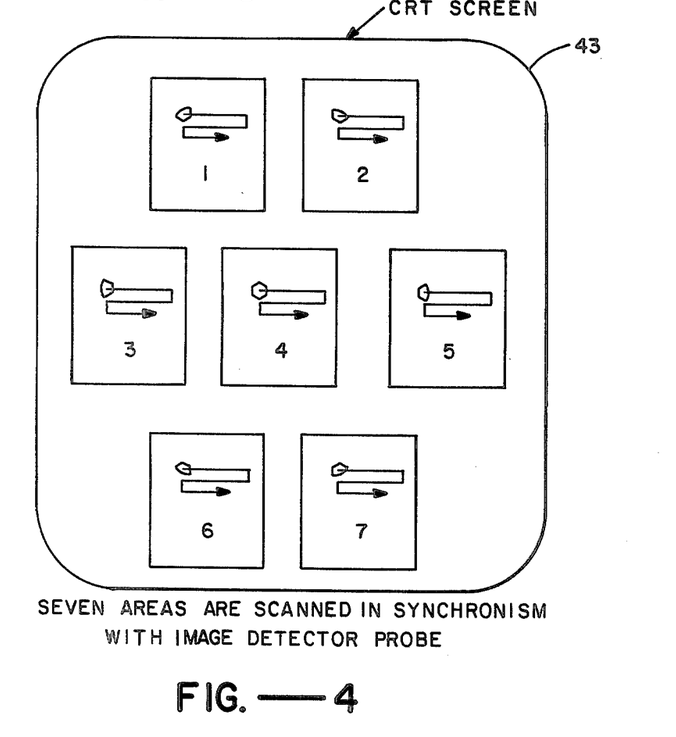
FIG. 4 shows the manner in which the cathode ray tube screen is scanned to obtain the multiple images.

This method of scanning in synchronism with the image detector probe is shown in FIG. 4 and shows the manner in which the seven different views are obtained. As shown therein, view No. 1 is entitled a right superior oblique, view No. 2 is identified as a left superior oblique, view No. 3 right oblique, view No. 4 normal, view No. 5, left oblique, view No. 6 right inferior oblique and view No. 7, left inferior oblique. A light sensitive medium in the form of a film 47 is provided for recording the information as it is scanned on the CRT screen 43 as viewed through the single lens 46.

More specifically, the electronic circuitry in block 21 includes analog computation circuitry as described in U.S. Pat. No. 3,011,057 that transforms the output signals from the phototubes into x and y signals that represent the x and y coordinates of each scintillation. These pulses are then analyzed in the multi-angle image display circuits by the use of conventional AND logic networks to divide the image detector field into the plurality of areas hereinbefore described. This is accomplished by way of example in delineating areas 1 and 2 by first establishing by the use of comparators and by setting the comparator levels to ascertain that the areas 1 and 2 are on opposite sides of the y axis. The tilted dividing lines for dividing the probe radiation image between areas 1 and 2 and areas 3, 4 and 5 are then obtained by adding x and y signals in the proper proportions to form new x and y signals having a tilted reference axis to delineate the remaining sides of areas 1 and 2. The other areas are delineated in a similar manner.

By utilizing conventional pulse height analyzing techniques, the pulses which are received can be readily analyzed to define in which area they appear merely by setting the levels of the comparators and thereafter using AND gate logic circuitry to define the specific area to which the pulse pertains. It can be seen that the circuitry thus far described is utilized for converting analog information into digital information. This digital information is carried by the AND gates and is strobed into latches which retain the information as to the area in which the pulses appeared. This digital information in the latches is then converted back to analog information in a conventional manner by a resistive network and then is supplied to the screen of the CRT which places the pulse information on the screen of the CRT in the same but minified area as received from the corresponding area of the crystal. At the same time information with respect to movement of the probe relative to the subject along x and y axes is supplied through an additional conventional resistive network which is combined with the resistive network connected to the latches to provide a slow sweep on the screen of the CRT corresponding to the relative travel between the probe and the subject. Thus it can be seen that the information supplied on the screen of the CRT will provide in each of the seven areas, the pulses which are received from the photomultiplier tubes from the corresponding areas of the crystal during the time that the scanning operation is taking place.

Figure 5:
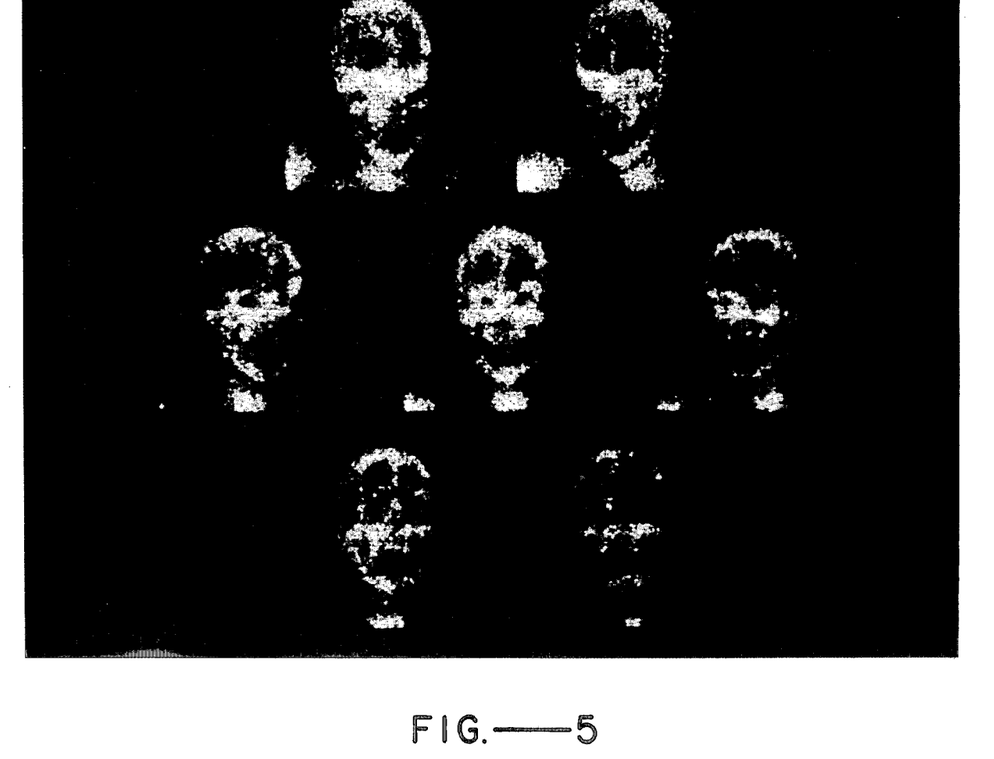
FIG. 5 is a photograph showing the multiple images which can be obtained utilizing the apparatus and method disclosed in FIG. 1.

In FIG. 5, there are shown seven views utilizing the present apparatus and method. They represent an anterior head scan of a patient who received Technetium EHDP. The center image is a normal anterior view, in other words, a non-oblique view. To the left and right of the center image are right and left oblique views with the angle between adjacent views being approximately 20° as represented by angles of the holes in the different portions of the focused collimator. The two top images are right and left superior views at 20° compound angles and the two bottom images are right and left inferior oblique views also at 20° compound angles. All these views were obtained simultaneously from a single scan at the same time that the conventional six tomographic readouts were obtained through the elements shown in block 17.

The method hereinbefore described provides the multi-angle readouts for the following reasons. The central area of the sodium iodide crystal looks at the patient through the central portion of the focused collimator 22 and since the holes in the central portion of the collimator are substantially vertical, the gamma rays detected in this area are all emitted from the patient in approximately a vertical direction and therefore they produce the normal anterior view of the subject or patient. The right hand portion of the sodium iodide crystal looks at the patient through the slanted holes on the right hand portion of the focused collimator where the holes are inclined an average of approximately 20° from the vertical. Therefore, the gamma rays detected in the right hand portion of the crystal are all emitted from the patient at approximately 20° angle and they therefore produce a 20° oblique view. Thus it can be seen that the six areas which surround the central area 4 on the edge of the crystal provide six images at six angles spaced in a hexagonal pattern about the normal view.

It should be appreciated that each multi-angle image has one seventh as many dots as the tomographic images because each detected gamma ray produces a dot in only one of the multi-angle images. This is in contrast to the tomographic readouts where each detected gamma ray produces a dot on all the images. Therefore, multi-image readouts tend to be statistics-limited in situations where the gamma ray flux is low.

Thus it can be seen from the embodiment of the invention shown in FIGS. 1-4 that the multi-angle readouts have been obtained by electronically dividing the probe radiation image provided by the scintillation crystal into seven areas and utilizing the counts in each area to form a separate image. The clinical value of the multi-angle oblique views lies in allowing the observer to see around overlying objects that might obscure deeper lying objects in the subject. In addition, they provide information on the relative depth of the objects. The multi-angle views are particularly valuable in bone scans and are expected to be very helpful in nearly all other kinds of organ and tumor scanning.

It should be appreciated in conjunction with the description shown in FIGS. 1-4 that if desired, the tomographic scanning capabilities can be eliminated and the multi-angle readouts can be provided from an independent apparatus. It also should be appreciated from the foregoing that the multi-angle image apparatus of the type shown in block 18 can be provided as a retrofit apparatus for use with tomographic scanners which are presently in the field. As can be seen, the invention is formed in such a manner that it can be readily adapted to existing tomographic scanners as well as being incorporated in new tomographic scanners. Alternatively, as pointed out above, the multi-angle readout can be provided as a separate and independent piece of apparatus merely by providing it with its own probe and x and y position information.

As pointed out above, in the embodiment of the invention shown in FIGS. 1-4, the multi-angle readouts are obtained by electronically dividing the radiation image field into a plurality of areas. In the embodiment of the invention shown in FIG. 6, the multi-angle views are obtained optically. This can be accomplished by modifying a multiple plane tomographic scanner of the type disclosed in U.S. Pat. No. 3,979,594. As described therein, as the probe scans the subject, the film in the optical readout camera scans in synchronism. By the use of several lenses with graded focal lengths, the six pictures each resolving a different plane within the subject are obtained from a single cathode ray tube display of the scintillations occurring in the probe. In place of the multiple lenses to show different images of different size on a piece of film, in FIG. 1 the images of different sizes are placed directly on a cathode ray tube using the electronic circuitry in block 24 so that the lens 29 and the film 31 can be stationary.

Figure 6:
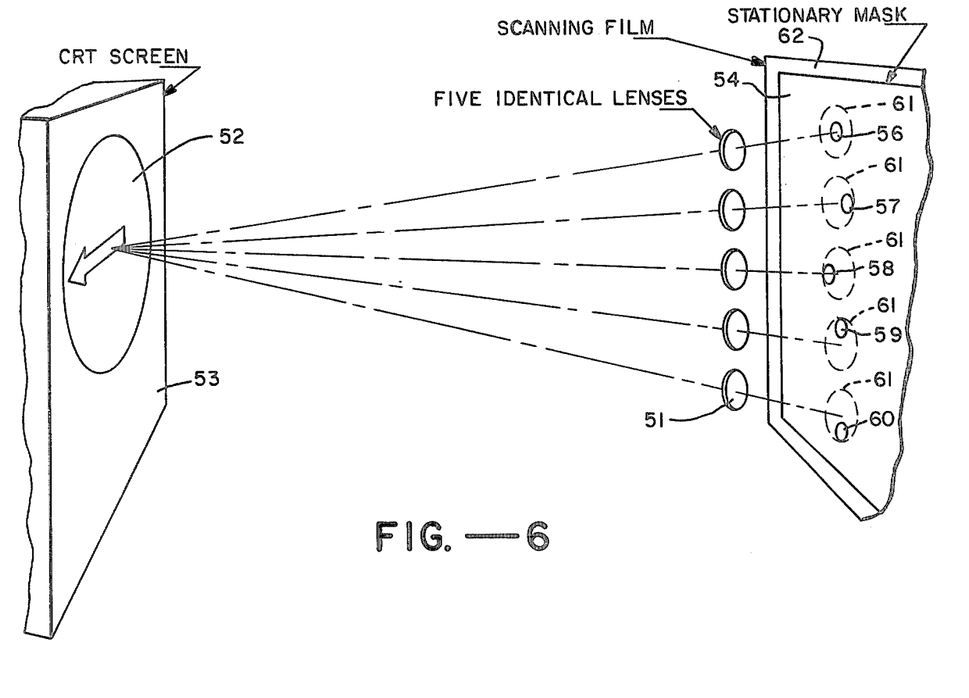
FIG. 6 is a schematic illustration of another embodiment of the present invention in which the multiple images are obtained by optically dividing the image detector field into a plurality of areas rather than electronically dividing the same as shown in the apparatus in FIGS. 1-4.

To obtain the multi-angle images optically rather than electronically, the six lenses of different focal lengths in the tomographic scanner are replaced by five identical lenses 51 which have the same focal length. The five lenses 51 receive optical information from the screen 52 of a cathode ray tube display apparatus 53. The CRT apparatus 53 is connected by electronic circuitry to the probe so that there is provided on the screen 52 optical images which have positions on the screen corresponding with the positions of the radiation images in the probe. A stationary mask 54 is provided which has a plurality of holes or apertures 56, 57, 58, 59 and 60 therein with the number of holes corresponding to the number of lenses. The holes or apertures 56 are much smaller as for example approximately one-half of the field 61 provided by the associated lens 51. It is important that the aperture be properly positioned with respect to the field of the lens. As shown in FIG. 6, the aperture 56 has been positioned so that it is in the center of the field so as to provide an image which would correspond to the front-on view of the subject. The aperture 57 has been positioned so as to give a right hand view of the subject, aperture 58 a left hand view of the subject, aperture 59 an upper view of the subject and aperture 60 a lower view of the subject. A light sensitive medium in the form of a scanning film 62 is provided for recording the images which pass through the apertures 56 through 60. Means is provided for causing the scanning film to move in synchronism with the relative movement between the probe and the subject to obtain the desired image on the film during a single scan of the patient.

In this manner, it is possible to obtain five images during this single scan. Pairs of the images can be viewed simultaneously to obtain a stereo readout. For example, a horizontal stereo readout can be obtained by using the left and right hand views and a vertical stereo readout can be obtained by reading the upper and lower or top and bottom images on the film. By utilizing a stereo readout, the depth of lesions and anatomic landmarks can be quickly visualized. In addition, the multi-angle images which are obtained in this manner are also useful in seeing around overlying objects as pointed out above with respect to the previous embodiment of the invention.

Figure 7:
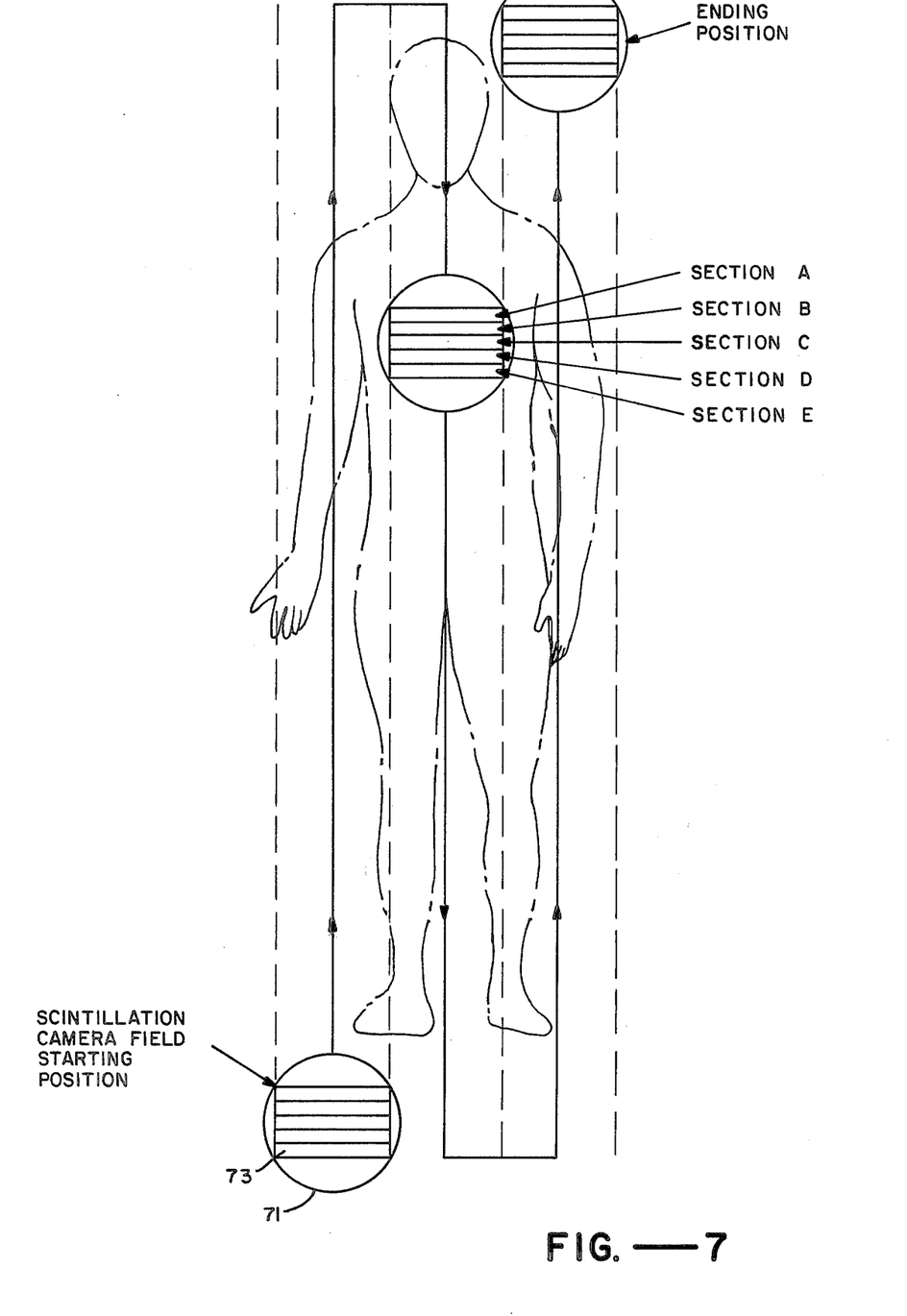
FIG. 7 is a diagramatic illustration showing the manner in which the present invention can be utilized in making a whole body scan.
Figure 8:
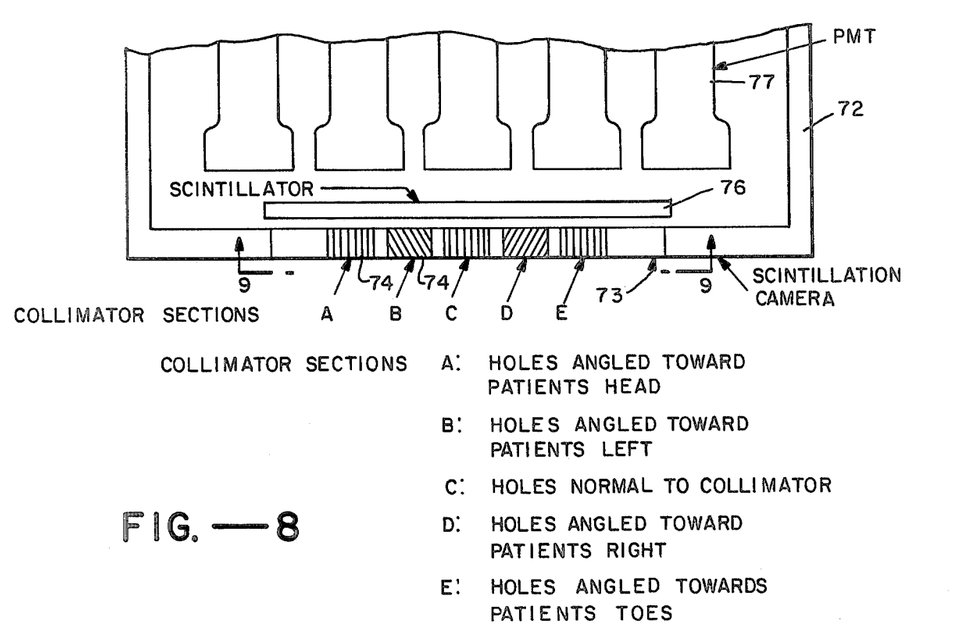
FIG. 8 is a partial cross-sectional view of the type of probe utilized in the apparatus for making a whole body scan.
Figure 9:
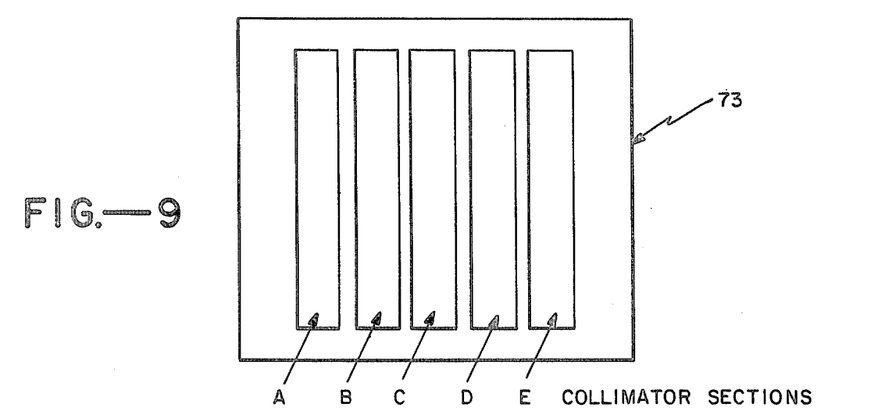
FIG. 9 is a bottom plan view of the collimator sections utilized in FIG. 8 looking along the line 9—9 of FIG. 8.
Figure 10:
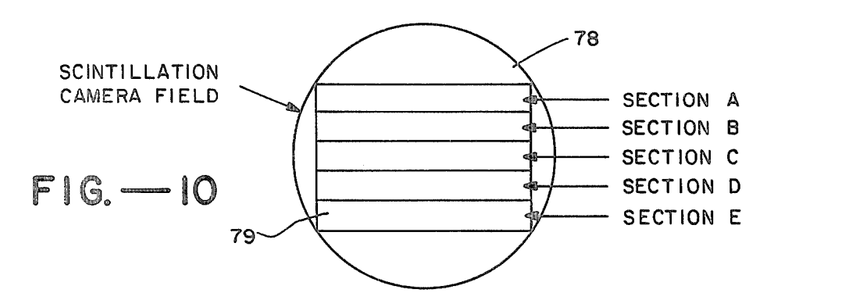
FIG. 10 is a plan view showing the scintillation camera field and the manner in which it is divided corresponding to the sections of the collimator.

Still another embodiment of the invention is shown in FIGS. 7-11. In the embodiments thus far described, a focused collimator has been utilized. In the present embodiment of the invention as hereinafter described, a special multi-section parallel hole collimator is utilized. The special collimator is utilized in a scintillation camera of the type described in U.S. Pat. No. 3,011,057 and a scanning table such as the Searle Scintiscan Model SS-10126A. The scintillation camera 71 (see FIG. 8) is provided with a housing 72 having a collimator assembly 73 mounted therein. The collimator assembly 73 is provided with a plurality of sections in excess of two as for example the five sections which are shown in FIGS. 8 and 9. Each of the sections is provided with a plurality of holes 74 as shown. As for example, the collimator section A is provided with parallel holes which are slanted toward the patient's head, section B is provided with parallel holes which are slanted toward the patient's left, section C is provided with parallel holes which are normal to the collimator, section D is provided with parallel holes which are slanted toward the patient's right and section E is provided with parallel holes which are slanted toward the patient's toes. The collimator assembly 73 is adapted to receive radiation in the form of gamma rays from the gamma ray radiating sources in the subject and permitting them to impinge upon a sodium iodide crystal 76 to cause scintillations therein. These scintillations are observed by a plurality of photomultiplier tubes 77 lying in an xy plane parallel to the plane of the crystal 76.

The scintillation camera when fitted with the special collimator assembly 73 hereinbefore described can be utilized in a whole body scanning system such as the Searle Scintiscan as hereinbefore described. When the scintillation camera is used in this manner, it can be described as a scintillation camera probe.

From the foregoing description, it can be seen that the special collimator has sections in it within which holes in each section are parallel to one another but that the holes in the different sections are at angle to one another. Means is provided in the whole body scanning system for causing relative movement between the scintillation camera probe and the subject. For this purpose, a very coarse scanning pattern can be utilized such as shown in FIG. 7 in which the probe 71 with its special collimator assembly 73 therein is moved relative to the patient or subject by first starting at the toes of the patient on the right side of the patient and scanning the right side of the patient. Relative movement between the probe 71 and the patient is then made so that the next scan will be over the middle portion of the patient and the last scan will be over the left side of the patient. Thus it can be seen that the whole body of the patient can be scanned by three passes of the probe relative to the patient. During the time that the scanning operation is taking place, a probe radiation image is provided from the scintillations occurring in the scintillator.

Figure 11:
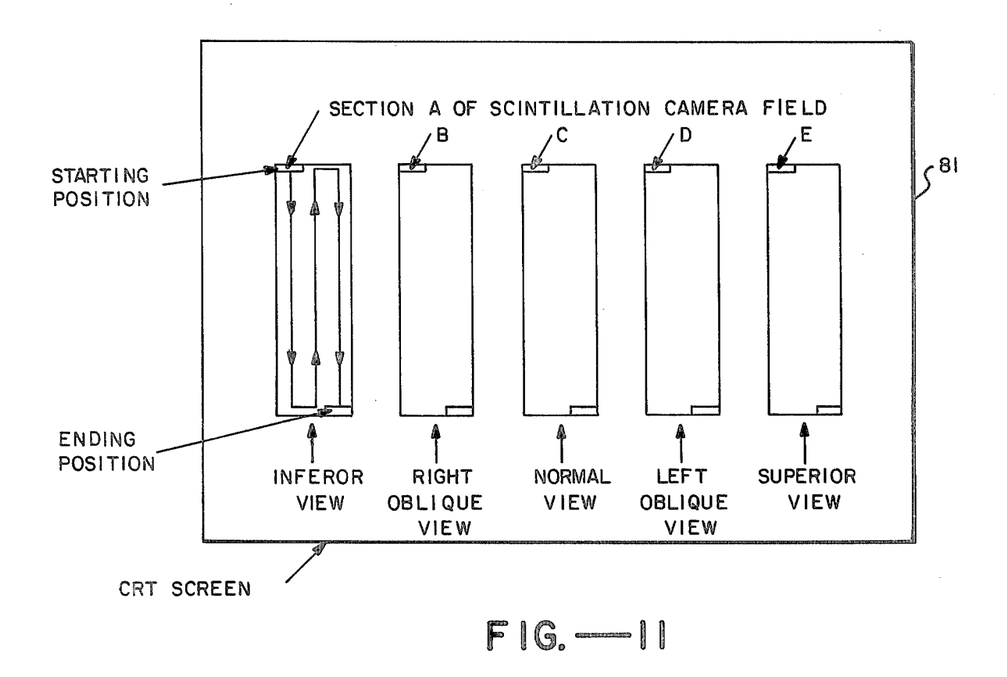
FIG. 11 is a view of the cathode ray tube screen showing the manner in which the sections are spaced apart and minified on the CRT screen and the manner in which scanning occurs on the CRT screen in synchronism with the scanning of the patient.

As with the embodiment of the invention shown in FIGS. 1-4, means is provided for electronically dividing the probe radiation image which also can be called the scintillator image into a plurality of sections 79 with each of the sections covering an area corresponding to the area occupied by a corresponding section of the collimator assembly 73. This electrical information is supplied onto the screen 81 as shown in FIG. 11. This electronic image moves on the screen 81 of the cathode ray tube in synchronism with the relative movement between the subject and the scintillation camera probe. The information on the screen 81 can then be recorded on a light sensitive medium such as film as described in the foregoing embodiments with the use of a single lens.

In order to utilize the present invention, the field of view of the scintillation camera probe 71 must be masked to a rectangular area as shown so that the information provided in the successive scans of the patient will be meaningful. The separate sections of the radiation image field are minified and are spaced apart as shown in FIG. 11.

It should be appreciated that in connection with the three linear head-to-toe passes, a typical subject can be covered. By way of example, a scintillation camera probe field which has been shielded to an 8 inch wide rectangular area can be utilized to sweep over the right hand portion of the subject, then index 8 inches to the left and sweep over the midportion, then index 8 more inches to the left and sweep over the left hand portion of the subject to complete the scan. The final result is five readouts of the scanned subject, each of which views the subject from a different angles. Thus it can be seen that the same type of information which was obtained in the previous embodiments can be obtained in the present embodiment. This is particularly advantageous for large objects. With the embodiment of the invention shown in FIGS. 1-4 and 6 as many as 300 left to right scanning motions would be required to cover a subject from head to toe in contrast to the three linear head to toe passes of the present embodiment.

It is apparent from the foregoing that there has been provided a multi-angle nulcear imaging apparatus and a method which makes it possible to obtain multi-angle readouts of the distribution of radiating sources. The multiple images can be utilized to see around superposed objects.

What is claimed is:

1. In a multi-angle nuclear imaging apparatus for obtaining a readout of a distribution of gamma-ray emitting radioactive material in a subject, a probe disposed in the vicinity of the subject for receiving radiation from the subject and forming a probe radiation image, said probe having a collimator with different portions thereof having holes disposed at different angles, a scintillator means overlying the collimator for receiving radiation passing through the collimator and producing scintillations to produce the probe radiation image, an array of photomultiplier tubes overlying the scintillator for detecting the scintillations and providing electrical outputs, a display apparatus having a cathode ray tube with a screen, means for converting the electrical outputs into optical images displayed on said screen, means for dividing the probe radiation image into a plurality of area, a light sensitive medium for receiving the optical images on said screen, means for causing relative movement between the probe and the subject for scanning said subject with said probe, and means for causing relative movement between the optical image and the light sensitive medium which corresponds to the relative movement between the probe and the subject whereby after scanning said subject there is produced on the light sensitive medium a plurality of non-overlapping images to portray the subject as seen from different angles.

2. Apparatus as in claim 1 wherein the means for dividing the probe radiation image into a plurality of areas and the means for causing relative movement between the optical images and the light sensitive medium is in the form of electronic circuitry.

3. Apparatus as in claim 1 wherein said means for dividing the probe radiation image into a plurality of areas includes a plurality of lenses having substantially identical focal lengths for receiving the optical images and providing image fields, a mask having an aperture therein for each of the lenses with the apertures having sizes substantially less than the sizes of the image fields provided by the lenses and with the apertures in the mask being positioned to provide the images on the light sensitive medium.

4. Apparatus as in claim 1 wherein said collimator is a focused colimator.

5. Apparatus as in claim 1 wherein said collimator is provided with a plurality of sections with each of the sections having parallel holes therein slanted at an angle which is different from the parallel holes in the other section of the collimator.

6. Apparatus as in claim 5 wherein said collimator has a rectangular field of view.

7. Apparatus as in claim 6 wherein said means for causing relative movement between the probe and the subject includes means for taking a whole body scan by scanning the subject from head-to-toe with at least two scans.

8. Apparatus as in claim 7 wherein one of the scans is on the right hand side of the patient and the other of the scans is on the left hand side of the patient.

9. An apparatus as in claim 1 wherein said areas include one central area and a plurality of peripheral areas located around said central area.

10. An apparatus as in claim 1 wherein said scintillator means consists solely of a single scintillator.

11. In a method for obtaining multi-angle readouts from a three dimensional distribution of gamma-ray emitting radioactive material in a subject by scanning of the subject with a probe having a collimator with portions thereof having holes therein at different angles, a scintillation crystal means overlying the collimator and an array of phototubes overlying the scintillation crystal, the method comprising producing a probe radiation image on the scintillation crystal from the gamma-ray radiation from said subject, converting the probe radiation image into optical images displayed on a screen, dividing the probe radiation image into a plurality of areas with the areas corresponding to the different portions of the collimator, recording the optical images on the screen onto a light sensitive medium, causing relative movement between the probe and the subject and causing relative movement between the optical images on the screen and the light sensitive medium corresponding to the relative movement between the probe and the subject whereby there is provided on the light sensitive medium a plurality of non-overlapping images to portray the subject as seen from different angles.

12. A method as in claim 11 wherein the dividing of the radiation image field into a plurality of areas is accomplished electronically.

13. A method as in claim 11 wherein the dividing of the radiation image field into a plurality of areas is accomplished optically.

14. A method as in claim 11 wherein the subject is a human body and wherein the relative movement is over the whole body.

15. A method as in claim 11 wherein said scintillator means consists solely of a single scintillator.

16. In a multi-angle nuclear imaging apparatus for obtaining a readout of the distribution of gamma-ray emitting radioactive material in a subject, a probe disposed in the vicinity of the subject for receiving gamma rays from the subject and forming a probe radiation image, said probe including a focused collimator, a scintillator overlying the focused collimator and receiving gamma rays passing through the focused collimator and producing scintillations to form the probe radiation image, an array of photomultiplier tubes overlying the scintillator and providing electrical outputs in response to the scintillations, x and y coordinate computing circuits connected to the outputs of the photomultiplier tubes and giving x and y coordinates for individual scintillations, electrical circuit means connected to the output of the x and y coordinate computing circuit for dividing the probe radiation image into a plurality of areas and producing first electrical outputs, means for causing relative movement between the probe and the subject in order to scan the subject and including means for producing second electrical outputs representing the x and y coordinates of the relative positions between the probe and subject, a cathode ray tube display apparatus having a screen, means for combining the first and second electrical outputs and supplying the same to the screen to provide on the screen a plurality of images corresponding to the areas of the probe radiation image, a lens for viewing the screen, a light sensitive medium receiving the images whereby there is provided on the light sensitive medium a plurality of non-overlapping final images which portray the subject as seen from different angles.

17. Apparatus as in claim 16 wherein the relative movement between the probe and the subject is a rectilinear scanning motion.

18. In a multi-angle nuclear imaging apparatus for obtaining a readout of a distribution of gamma-ray emitting radioactive material in a subject, a probe disposed in the vicinity of the subject for receiving radiation from the subject and forming a probe radiation image, said probe having a collimator with different portions thereof having holes disposed at different angles, scintillator means overlying the collimator for receiving radiation passing through the collimator and producing scintillations to produce the probe radiation image, an array of photo multiplier tubes overlying the scintillator for detecting the scintillations and providing electrical outputs, a display apparatus having a cathode ray tube with a screen, means for converting the electrical outputs into optical images displayed on said screen, means for dividing the probe radiation image into a plurality of areas including a plurality of lenses having substantially identical local lengths for receiving the optical images and providing image fields, a mask having an aperture therein for each of the lenses with the apertures having sizes substantially less than the sizes of the image fields provided by the lenses and which the apertures in the mask being positioned to provide the images on the light sensitive medium, a light sensitive medium for receiving the optical images on said screen, means for causing relative movement between the probe and the subject, and means for causing relative movement between the optical image and the light sensitive medium which corresponds to the relative movement between the probe and the subject whereby there is produced on the light sensitive medium a plurality of images of the probe radiation image to portray the subject as seen from different angles.

19. In a method for obtaining multi-angle readouts from a three dimensional distribution of gamma-ray emitting radioactive material in a subject by scanning of the subject with a probe having a collimator with portions thereof having holes therein at different angles, scintillation crystal means overlying the collimator and an array of phototubes overlying the scintillation crystal means, the method comprising producing a probe radiation image on the scintillation crystal means from the gamma-ray radiation from said subject, converting the probe radiation image into optical images displayed on a screen, optically dividing the probe radiation image into a plurality of areas with the areas corresponding to the different portions of the collimator, recording the optical images on the screen onto a light sensitive medium, causing relative movement between the probe and the subject and causing relative movement between the optical images on the screen and the light sensitive medium corresponding to the relative movement between the probe and the subject whereby there is provided on the light sensitive medium a plurality of images of the probe radiation image to portray the subject as seen from different angles.

20. In a multi-angle nuclear imaging apparatus for obtaining a readout of a distribution of gamma-ray emitting radioactive material in a subject, a probe disclosed in the vicinity of the subject for receiving radiation from the subject and forming a probe radiation image, said probe having a collimator with different portions thereof having holes disposed at different angles, a scintillator overlying the collimator for receiving radiation passing through the collimator and producing scintillations to produce the probe radiation image, an array of photomultiplier tubes overlying the scintillator for detecting the scintillations and providing electrical outputs, a display apparatus having a cathode ray tube with a screen, means for converting the electrical outputs into optical images displayed on said screen, optical means for dividing the probe radiation image into a plurality of areas, a light sensitive medium for receiving the optical images on said screen, means for causing relative movement between the probe and the subject, and means for causing relative movement between the optical image and the light sensitive medium which corresponds to the relative movement between the probe and the subject whereby there is produced on the light sensitive medium a plurality of images of the probe radiation image to portray the subject as seen from different angles.

* * * * *